United States Patent [19]
de la Torre

[11] Patent Number: 5,472,446
[45] Date of Patent: * Dec. 5, 1995

[54] SURGICAL INSTRUMENT FOR TYING A KNOT IN A LENGTH OF SUTURE AT A REMOTE LOCATION

[76] Inventor: Roger A. de la Torre, 48 Dauphine Dr., Lake St. Louis, Mo. 63367

[*] Notice: The portion of the term of this patent subsequent to Feb. 21, 2012, has been disclaimed.

[21] Appl. No.: 139,928

[22] Filed: Oct. 20, 1993

Related U.S. Application Data

[63] Continuation-in-part of Ser. No. 71,297, Jun. 2, 1993, Pat. No. 5,391,176.

[51] Int. Cl.⁶ ................................................. A61B 17/00
[52] U.S. Cl. .................... 606/148; 606/139; 606/144; 289/17
[58] Field of Search ............................. 606/1, 139, 144, 606/145, 147, 148; 112/169, 80.03; 289/17

[56] References Cited

U.S. PATENT DOCUMENTS

| | | |
|---|---|---|
| 1,400,653 | 12/1921 | Barbour . |
| 2,012,776 | 8/1935 | Roeder . |
| 2,455,833 | 12/1948 | Trombetta ................................ 289/17 |
| 2,566,625 | 9/1951 | Nagelmann ............................ 606/147 |
| 2,595,086 | 4/1952 | Larzelere . |
| 3,856,018 | 12/1974 | Perisse et al. . |
| 3,985,138 | 10/1976 | Jarvik . |
| 4,602,635 | 7/1986 | Mulhollan et al. . |
| 4,961,741 | 10/1990 | Hayhurst . |
| 5,084,058 | 1/1992 | Li . |
| 5,087,263 | 2/1992 | Li . |
| 5,129,912 | 7/1992 | Noda et al. . |
| 5,133,723 | 7/1992 | Li et al. . |
| 5,163,946 | 11/1992 | Li . |
| 5,211,650 | 5/1993 | Noda . |
| 5,217,470 | 6/1993 | Weston ................................... 606/148 |
| 5,234,443 | 8/1993 | Phan et al. ............................. 606/148 |
| 5,242,459 | 9/1993 | Buelna . |
| 5,312,423 | 5/1994 | Rosenbluth et al. .................... 606/148 |
| 5,405,352 | 4/1995 | Weston . |

*Primary Examiner*—Stephen C. Pellegrino
*Assistant Examiner*—Jeffrey A. Schmidt
*Attorney, Agent, or Firm*—Rogers, Howell & Haferkamp

[57] ABSTRACT

A surgical instrument and its method of use facilitate tying of a knot in a length of suture material at a remote surgical location. The instrument is comprised of a rod having a length of suture wrapped over the rod in a particular pattern. A needle is secured to a free end of the suture and the pattern of wrapping the suture on the rod enables loops of suture to move off the rod end and over the needle and suture to form a knot in the suture.

14 Claims, 7 Drawing Sheets

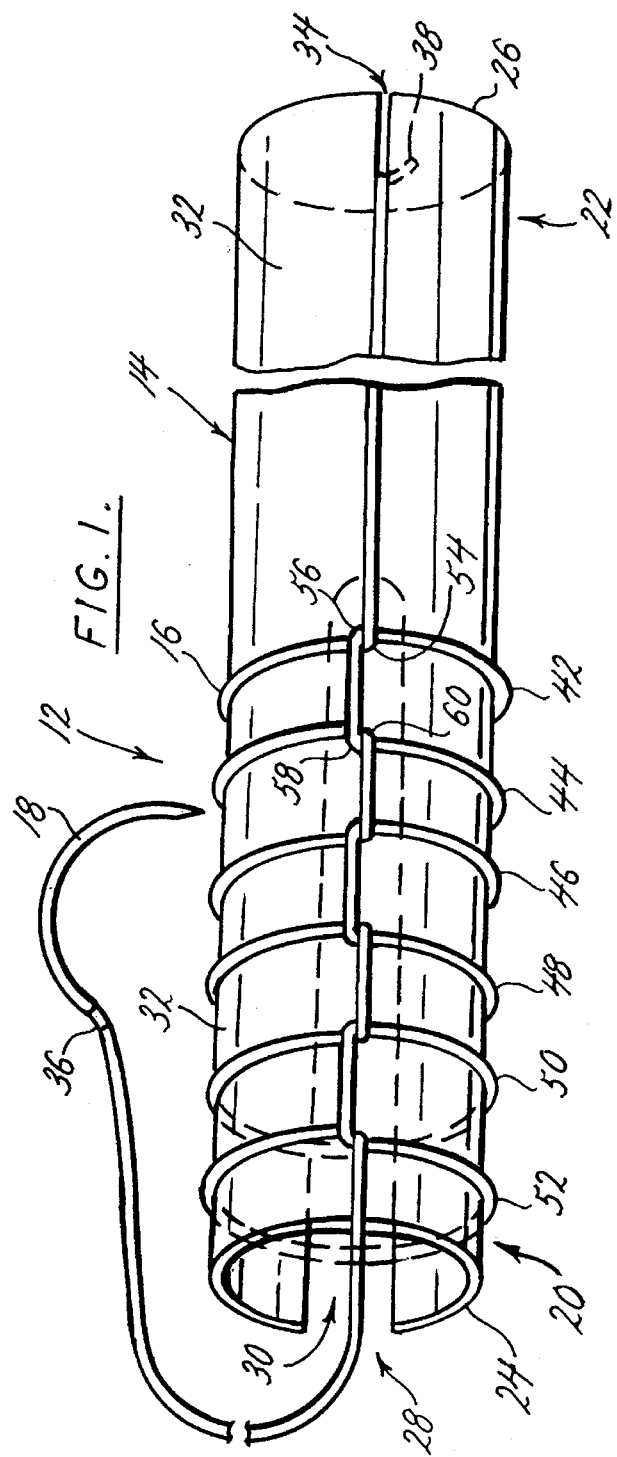
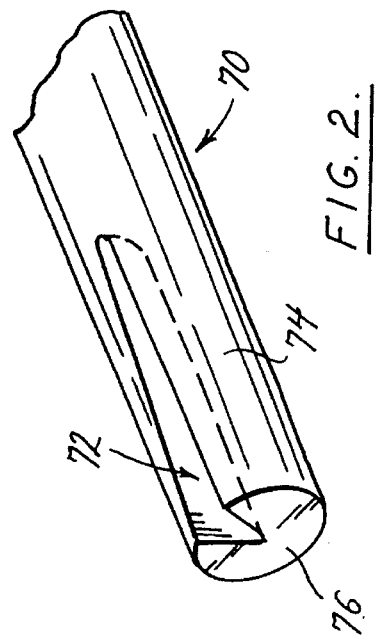

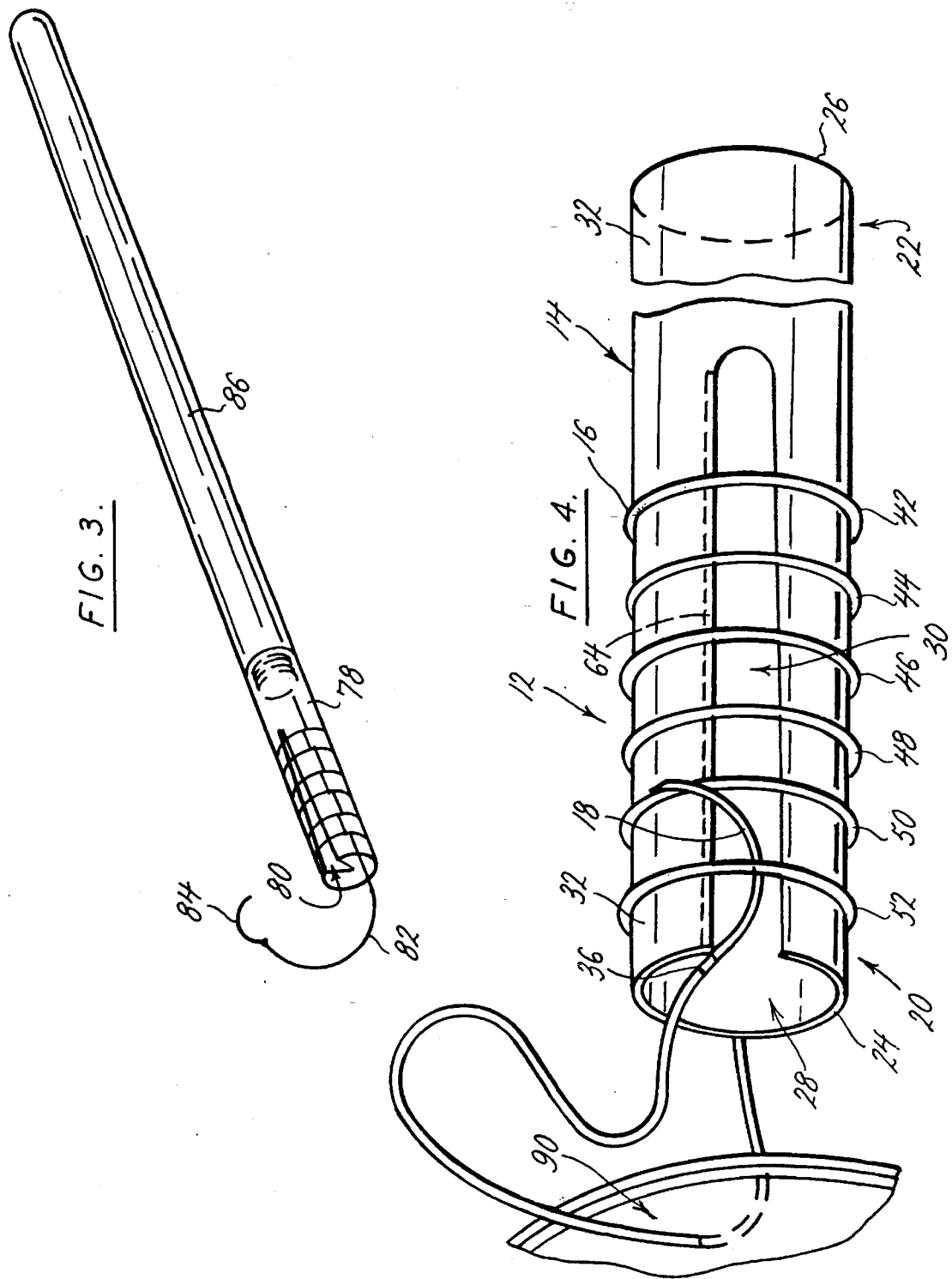

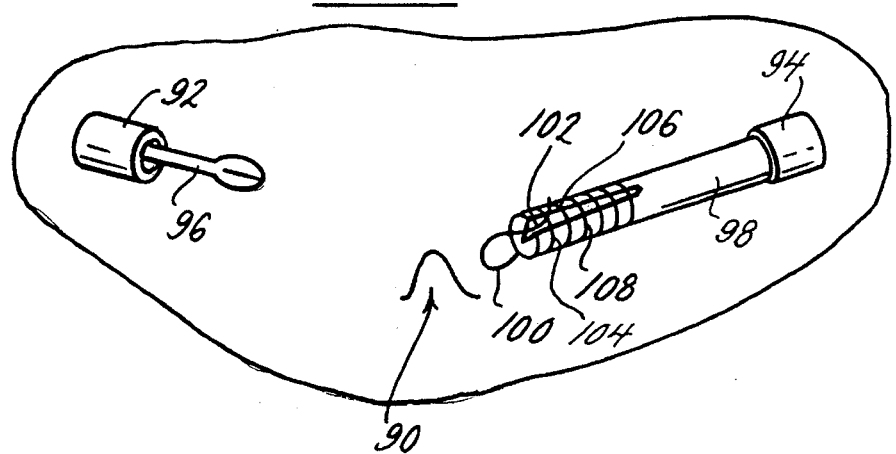
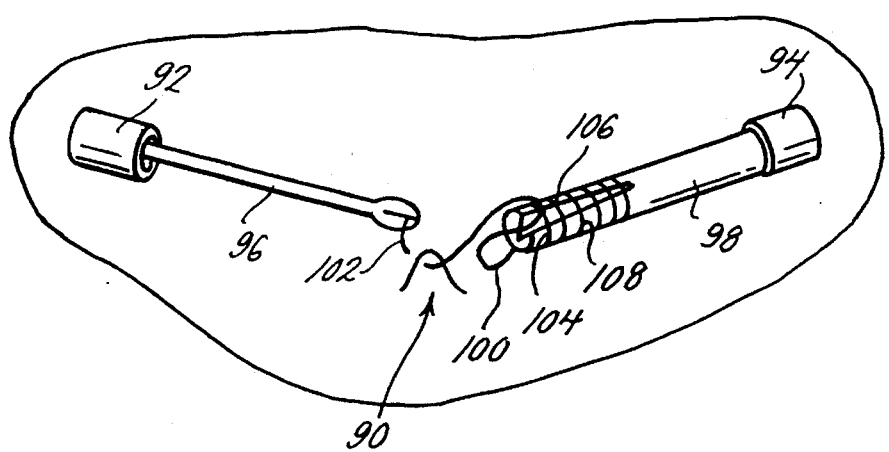
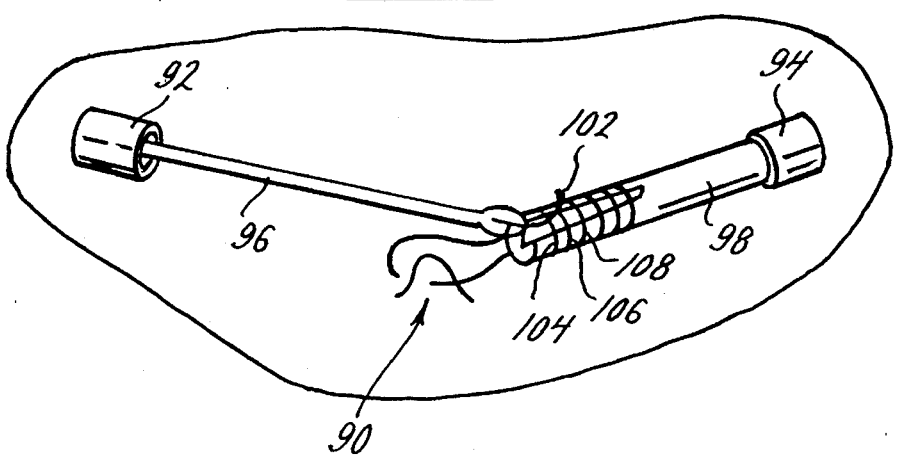

SURGICAL INSTRUMENT FOR TYING A KNOT IN A LENGTH OF SUTURE AT A REMOTE LOCATION

This is a continuation-in-part application of patent application Ser. No. 08/071,297, filed Jun. 2, 1993 and now U.S. Pat. No. 5,391,176.

BACKGROUND OF THE INVENTION

1. Field of the Invention

The present invention pertains to embodiments of a surgical instrument for tying a knot in a length of suture at a remote location and the methods of using the instruments in tying the knot.

2. Description of the Related Art

Various different types of instruments are known in the prior art for use in tying knots in lengths of suture material. Many of these prior art instruments have been developed with the intent to facilitate tying knots in suture material at surgical sites located in remote areas that are difficult to access. Many prior art instruments are designed for use in surgical procedures where large, deep incisions are made into the body. The instruments enable tying knots in sutures deep in the incisions. Many prior art instruments are also designed for use in laparoscopic surgical procedures where small incisions are made and the remote surgical site is accessed through cannulas or tubes. Examples of known instruments employed in tying knots in lengths of suture material are disclosed in the Larzelere U.S. Pat. No. 2,595,086, Mulhollan et al. U.S. Pat. No. 4,602,635, Hayhurst U.S. Pat. No. 4,961,741, the Li U.S. Pat. Nos. 5,084,058; 5,087,263; and 5,163,946; and the Li U.S. Pat. No. 5,133,723.

A common characteristic of many known surgical knot-tying instruments is that they are very complicated to operate and time consuming to set up prior to their use. Moreover, many prior art surgical knot-tying instruments are used in a procedure that involves first tying the knot in a length of suture remote from the surgical location and then moving the loose knot along the length of suture material to a position proximate to the surgical location before the knot is tightened at the surgical location.

SUMMARY OF THE INVENTION

The present invention overcomes disadvantages commonly associated with prior art surgical knot-tying instruments by providing embodiments of a simplified surgical instrument for tying a knot in a length of suture proximate to a surgical site. More specifically, the surgical instrument of the present invention may be employed in either open incision or laparoscopic surgery procedures to position a needle and a length of suture material proximate to a surgical location and to form one or more stitches with the length of suture material at the surgical location, and then to tie a knot in the length of suture material at the surgical location where the knot is formed from two or more throws of the suture material.

The instrument is basically comprised of an elongate rod having opposite first and second ends. The longitudinal length of the rod is designed to enable the first end of the rod to be inserted through a conventional, laparoscopic cannula to position the rod first end proximate to a surgical location or site within a body cavity accessible by the cannula. The second end of the rod projects from the cannula where it is grasped manually to enable manipulation of the rod first end within the body cavity. In alternate embodiments of the invention, the rod has a shortened longitudinal length and is connected to an elongate handle that enables manipulation of the rod within the body cavity through a cannula by manual manipulation of the handle. In this embodiment of the invention, the rod is detachable from the handle for its removal and disposal after use and replacement by a like rod on the handle.

In one embodiment, the first end of the rod is provided with an indentation or slot that extends into the interior of the rod from the rod's exterior surface. A length of suture material is provided on the rod first end. The length of suture has a needle secured to its first end and the second end of the suture is secured to the second end of the rod or to the handle. The length of suture is wrapped around the first end of the rod in a specific pattern that provides a plurality of loops of the suture material around the first end extending over the slot formed in the rod. A portion of the suture's length extends from the last of the plurality of suture loops formed on the rod first end to the needle at the first end of the suture.

Means are provided on the first end of the rod for releasably holding the needle to the rod first end. In the preferred embodiment, a magnet is encased in the material of the rod adjacent the rod first end. The magnet attracts the needle to the rod end and holds the needle in position on the rod end where it may be easily removed.

In use, the first end of the rod is positioned proximate to a surgical location by inserting the rod end into an open incision or by inserting the rod first end through the interior of a cannula providing access to a body cavity. With the first end of the rod positioned proximate to the surgical location, the needle is removed from its magnetic attachment to the rod either manually or by gripping the needle with a laparoscopic grasper. One or more stitches are made in the desired positions at the surgical location and in preparation to form a first throw of a knot in the suture material, the needle is inserted into the slot in the rod first end beneath the first loop of suture material formed on the rod end. The needle is held in this position beneath the first loop of suture by the magnetism of the rod first end. The needle is released by the grasper and then retaken by the grasper at the distal end of the needle projecting from beneath the first suture loop. The needle and the first end of the suture material are then pulled from the slot and from beneath the first suture loop causing the first loop to move off the first end of the rod. As the needle and first end of the suture are continued to be pulled away from the rod first end, the first loop moves down the length of suture toward the stitch made at the surgical location, forming a first throw of a knot in the suture material securely closing the stitch. This procedure may be repeated as many times as there are suture loops formed on the rod first end to form a knot of any desired number of throws. When the desired knot is formed at the stitch in the surgical location the two lengths of suture extending from the knot are cut and the knot-tying instrument and needle are removed from the surgical location.

In an alternate embodiment the rod has a hollow interior bore extending between its first and second ends and there is no slot or recess formed at the first end of the rod. The length of suture, having a needle secured to its first end and the second end secured to the second end of the rod or handle, is wrapped around the first end of the rod in a specific pattern, different from the pattern of wrapping of the first embodiment. The suture material extends from the wrapping to the needle, and the needle and the portion of the suture connected to the needle may be stored in the interior bore of the rod for insertion of the rod through the interior of a cannula. The interior bore of the rod is dimensioned sufficiently large to enable a conventional surgical grasper to pass through the interior bore with the grasper clamping the needle for manipulation of the needle from the rod first end.

The use of this variant embodiment is similar to that of the first described embodiment. The first end of the rod is positioned proximate to a surgical location by inserting the rod through the interior of a cannula. The needle is removed from the rod interior bore by a conventional grasper inserted through the bore from the second end of the rod. The grasper, clamped to the needle, is manipulated through the interior bore of the rod and out of the rod first end to pass the needle through tissue at the surgical location in forming a first stitch in the tissue. The needle is then released by the grasper and the grasper then grips the distal end of the needle passed through the tissue and pulls the needle and the suture material attached to the needle through the tissue in forming the first stitch. The grasper then pulls the needle and the suture material back into and through the interior bore of the rod. As the suture material is pulled back through the interior bore of the rod, the plurality of loops of suture material formed on the exterior surface of the rod first end are pulled off the rod first end and over the portion of suture being pulled back into the interior bore of the rod. A second grasper may be used to facilitate passing the plurality of loops of suture material off the rod first ends and over the portion of suture being pulled back into the rod interior bore. As the surgical grasper continues to pull the needle and attached portion of suture material through the rod bore from the rod first end toward the rod second end, the loops of suture material now wrapped around the portion of suture being pulled into the rod bore contract over that portion of suture and form a knot in the suture at the surgical location. After formation of the knot in the suture material at the suture location, the two lengths of suture extending from the knot are cut and the knot-tying instrument and needle are removed from the surgical location.

BRIEF DESCRIPTION OF THE DRAWINGS

Further objects and features of the present invention are revealed in the following detailed description of the preferred embodiments of the invention and in the drawing figures wherein:

FIG. 1 shows a fragmented perspective view of the surgical instrument for tying a knot in a length of suture;

FIG. 2 shows a partial perspective view of a variant embodiment of the instrument of the invention;

FIG. 3 shows a perspective view of a still further embodiment of the instrument of the invention;

FIG. 4 shows a fragmented perspective view similar to that of FIG. 1 with the instrument of the invention rotated 180°;

FIG. 5 is a schematic representation of a step involved in the method of use of the instrument of the invention in tying a knot in a length of suture in laparoscopic surgery;

FIG. 6 is a subsequent step to that shown in FIG. 5;

FIG. 7 is a subsequent step to that shown in FIG. 6;

DESCRIPTION OF THE PREFERRED EMBODIMENTS

Figure 8:
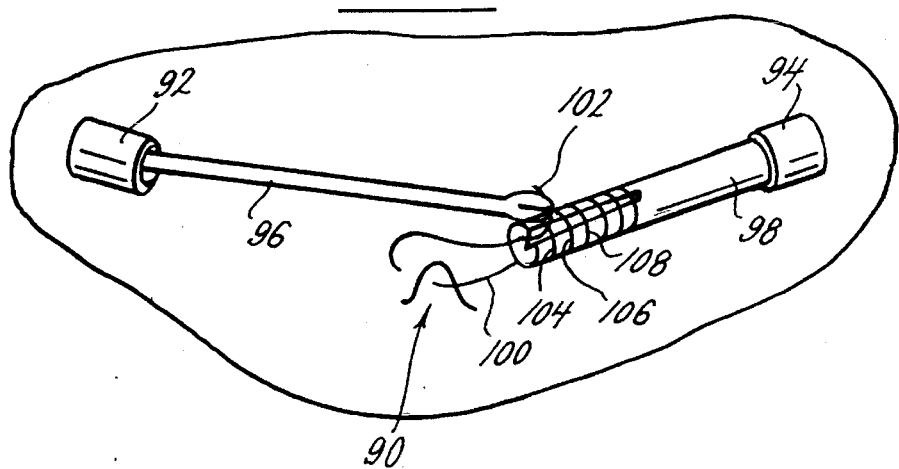
FIG. 8 is a subsequent step to that shown in FIG. 7.

A first embodiment of the surgical instrument 12 of the present invention is shown in FIGS. 1 and 4. This first to be described embodiment of the invention, as well as other embodiments of the invention yet to be described, may be constructed of any materials acceptable for use in surgical operations. The instrument is basically comprised of an elongate rod 14, a length of suture material 16 secured to the rod, and a needle 18 secured to the length of suture material.

The elongate rod has opposite first 20 and second 22 ends, or left hand and right hand ends respectively, adjacent opposite first 24 and second 26 end faces, or left and right end faces, as viewed in FIGS. 1 and 4. A hollow interior bore 28 extends longitudinally through the rod 14 between its end faces 24, 26. The interior and exterior diameter dimensions of the rod 14, as well as its longitudinal length between end faces, may vary depending on the intended application of the instrument. The instrument is designed for use with both open incision surgery and laparoscopic surgery and the rod 14 of the instrument may be dimensioned so that it can be easily inserted through the interior of a cannula in laparoscopic surgery applications. Additionally, the lateral dimensions of the instrument rod 14 may be enlarged to further facilitate its use in open incision surgical operations. The dimensions of the rod 14, suture material 16, and needle 18 shown in the drawing figures are not to scale and are not proportionate but are enlarged in FIGS. 1 and 4 to better illustrate the component parts of the invention and their relationship to each other. Moreover, it is not necessary that the instrument rod have the cylindrical configuration shown in FIGS. 1 and 4.

A slot 30 is formed through the exterior surface 32 of the rod adjacent its first end 20 forming a recess or indentation into the rod from the exterior surface to the interior bore 28. As seen in the drawing figures, the slot 30 extends longitudinally from the first end face 24 of the rod along a portion of the rod's length. A second smaller slot 34 or slit is formed in the second end 22 of the instrument rod extending along a portion of the longitudinal length of the rod from the second end face 26.

The length of suture material 16 has opposite first 36 and second 38 ends with the first end 36 of suture material being secured to the needle 18 in a conventional manner. The total length of the suture material between its first and second ends may vary depending on the intended application of the surgical instrument of the invention, as will be explained. The second end 38 of the suture is secured adjacent the rod second end 26 by inserting the suture into the narrow slot 34. In variant embodiments of the invention, the second end 38 of the suture may be secured to the instrument rod 14 in any equivalent manner, or may be manually held adjacent the rod second end in use of the surgical instrument. The length of suture 16 extends from the instrument rod second end 22 along the exterior surface of the rod toward the rod first end 20 and is wrapped in several loops 42, 44, 46, 48, 50, 52 at the first end 20 of the rod. From the last of the plurality of loops, the suture material extends to its first end 36 secured to the needle 18.

As best seen in FIG. 1, each of the loops of suture material are wrapped around the exterior surface of the rod in a specific configuration that enables individual loops to be spaced from each other along the rod first end 20 and also enables individual loops to be manipulated to slide along the longitudinal length of the rod first end without causing adjacent loops to move along the length of the rod. Although a specific arrangement of the suture material to form the plurality of loops is shown in FIG. 1, it should be appreciated that the suture material 16 may be formed in a variety of different loop configurations on the rod first end 20 that enable the plurality of suture loops to be spaced from each other as shown in FIG. 1 and allow individual loops of suture material to be manually moved longitudinally over the exterior surface of the rod without causing adjacent loops to be moved.

The specific configuration of the suture loops shown in FIG. 1 is produced by forming a first bend 54 in the suture material 16 as it extends longitudinally over the exterior surface of the rod 14 from the second end 22 toward the first end 20 of the rod. From the first bend 54, the suture material extends laterally relative to the rod and is wrapped one complete revolution around the exterior surface of the rod back to the first bend 54. The suture material is then formed in a second bend 56 around the first bend 54 of the suture and again extends longitudinally along a portion of the rod's length, thereby completing the formation of the first loop 42 in the suture material. The subsequent or adjacent loop 44 is formed in substantially the same manner as the first described loop 42. In forming the second loop, a first bend 58 is formed in the suture material and the suture extends from the first bend laterally around the exterior surface of the rod 14 one complete revolution back to the first bend of the second loop. Next, a second bend 60 is formed in the suture material around the first bend 58 of the second loop. The suture material continues to extend longitudinally toward the rod first end 20 from the second bend 60, thereby completing the second loop 44 of suture material formed on the exterior of the rod 14. The remaining pairs of loops 46 and 48, 50 and 52, are formed in the suture material as it extends toward the rod first end 20 in the identical manner as the first pair of loops 42, 44 just described.

To illustrate that the loops of suture material formed over the exterior surface of the rod 14 may be formed in a variety of different configurations without departing from the intended scope of the claims of the invention, it is noted that the first and second loops 42, 44 are substantially mirror images of each other, and the second and third loops 44, 46 are also substantially mirror images of each other. In variations of the invention, these first three loops of suture material may have been wound around the exterior surface of the rod 14 so that their configurations are substantially identical to each other, as are the first and third loops 42, 46. Moreover, all of the loops of suture material could have been wrapped around the exterior of the rod 14 in substantially the same configuration as the first loop 42 or all of the plurality of loops could have been wrapped in substantially the same configuration as the second loop 44 without departing from the intended scope of the claimed invention and without altering the operation of the invention or its method of use.

To prevent the plurality of suture loops from unraveling from the rod first end 20 and to prevent the needle 18 from hanging free from the rod first end a strip magnet 64 is encased in the material of the rod first end extending along one side of the first slot 30 as shown in FIG. 4. By positioning the needle 18 adjacent the side of the slot 30 having the strip magnet 64, the needle is held securely in place at the rod first end 20 as shown in FIG. 4. Alternate means of securing the needle 18 at the rod first end 20 may be employed in place of the strip magnet 64. For example, the rod first end 20 may be formed without the strip magnet 64 and the needle 18 may be positioned between the suture loop 52 formed adjacent the rod first end face 24 and the exterior surface 32 of the rod to securely hold the needle in place. To prevent the needle tip from projecting from the rod first end the needle may be given a curvature substantially equal to that of the rod exterior surface so that it may be positioned beneath the end loop 52 extending adjacent the rod exterior surface to its tip.

In variant embodiments of the instrument rod 14 the strip magnet 64 could be eliminated from its position adjacent the slot 30 and the needle 18 could be held in place relative to the rod by a conventional laparoscopic surgery grasper inserted through the rod interior bore 28 from its second end 22. The exterior diameter of the rod 14 would be dimensioned small enough to enable it to be inserted through the interior of a conventional laparoscopic cannula. The interior diameter of the rod bore 28 would be dimensioned sufficiently large to enable the insertion of a conventional laparoscopic grasper through the bore. The grasper would be inserted through the rod bore from the rod second end 22 with the jaws of the grasper positioned adjacent the rod first end 20. In this position of the grasper, the Jaws would grip and releasably hold the needle 18 on insertion of the first end of the instrument rod through the cannula into the body cavity, and in subsequent manipulations of the needle in forming throws of a knot according to the method of the invention yet to be described. Using the surgical instrument of the invention 12 in this manner also provides the surgeon with a pair of laparoscopic graspers to use together with the instrument in forming stitches laparoscopically without the requirement of inserting more than a pair of cannulas into the body cavity.

In the illustrated embodiment of the invention shown in FIGS. 1 and 4, six suture loops are formed in a length of suture material, and the longitudinal length of the first slot 30 is extended along the length of the rod so that it passes beneath each of the loops formed in the suture material. In variant embodiments of the invention, the number of suture loops may vary and the longitudinal length of the slot beneath the loops may also vary. In use of the invention, it is only necessary that the longitudinal length of the slot be sufficient to enable each of the plurality of loops formed in the suture material to extend over the slot.

FIG. 2 shows a variant embodiment of the rod 70 of the surgical instrument. In this embodiment, the rod again has a cylindrical configuration; however, the rod does not have a hollow interior bore as in the first embodiment. The rod configuration shown in FIG. 2 is solid with the slot 72 extending down into the interior of the material of the rod from the exterior surface 74. The slot 72, like the slot of the first embodiment, extends for a portion of the longitudinal length of the rod from the rod first end face 76. The longitudinal length of the slot 72 is determined to enable the slot to extend beneath the plurality of loops formed in suture material (not shown) wrapped over the first end of the rod 70. The remaining component parts, i.e. the suture material and needle, of the second embodiment of the surgical instrument employing the solid rod 70 are substantially identical to those of the first described embodiment of FIGS. 1 and 4.

FIG. 3 shows a still further variant embodiment of the surgical instrument rod 78. In the embodiment of the rod 78 shown in FIG. 3, the first end, or left hand end of the rod as viewed in FIG. 3, may have the same tubular configuration of the first described embodiment of FIGS. 1 and 4 or may have the solid configuration of the rod shown in FIG. 2. The rod has a slot 80 formed in its first end in the same manner as the previously described embodiments and a length of suture material is wrapped over the exterior surface of the rod and the slot with one end of the suture secured to the rod and the opposite end of the suture secured to a needle 82 in the same manner as the first described embodiments. The embodiment of FIG. 3 differs from the previously described embodiments in that the longitudinal length of the surgical instrument is divided into two sections with the first section comprising the rod 78 and the second section comprising a handle 86. As shown in FIG. 3, the second end of the rod 78 is detachably secured to one end of the handle 86 by a threaded connection 88. Other equivalent means of providing a releasable connection may also be employed. In this embodiment of the invention, the longitudinal length of the instrument enables it to be used in both deep open incisions or in laparoscopic surgery as in the previously described embodiments. The ability of the rod 78 to be detached from the handle 86 enables the rod to be detached and disposed of after use and replaced on the handle by a like rod. With the configuration of the surgical instrument shown in FIG. 3, once the length of suture has been used from one rod of the instrument the used rod may be detached from the handle and replaced with a new rod having a length of suture looped over its exterior surface.

FIGS. 5–10 are schematic representations of the method of the invention employed in using the surgical instrument of the invention for tying a knot in a length of suture in a laparoscopic surgical operation. The drawing figures and their descriptions to follow only generally describe one use of the surgical instrument of the invention and are employed only to illustrate some benefits provided by the surgical instrument of the invention. Drawing FIGS. 5–10 and their descriptions to follow describe use of the surgical instrument of the invention in laparoscopic surgery forming a single stitch to close an incision. Again, it should be understood that the description to follow is illustrative only and should not be interpreted as limiting the use of the surgical instrument of the invention to only laparoscopic surgical techniques or only use in forming one stitch in securing adjacent tissues together. The benefits provided by the unique surgical instrument of the present invention suit it for use in a variety of different known surgical techniques and for use in forming both a single stitch and a line of stitching in body tissues.

FIG. 5 is a schematic representation of a view looking inside a body cavity toward an opening in a tissue 90 representing a defect to be repaired or mended by use of the surgical instrument of the invention in accordance with the method of the invention. The drawing figure and FIGS. 6–10 to follow illustrate a laparoscopic repair of the defect 90 in the tissue and a pair of trocars 92, 94 are shown already inserted through left and right flanks of the body into the cavity, respectively. Graspers 96 are shown inserted through the left trocar 92 into the body cavity and the first end of the surgical instrument rod 98 with the length of suture 100 wrapped thereover and the needle 102 secured to the suture are shown inserted through the right trocar 94. The needle 102 is shown releasably held to the first end of the instrument rod 98 by a magnet encapsulated in the material of the rod, as was explained earlier. The length of suture extending from the needle 102 to the first suture loop 104 formed on the rod end may be longer than that shown in FIG. 5 to facilitate manipulation of the needle in producing a stitch through the defective tissue 90. The excess length of suture between the needle 102 and the first suture loop 104 may be spirally wound on the rod first end between the rod end face 106 and the first loop 104. In preparing to use the instrument of the invention, the second end of the rod 98 (not shown) extending from the exterior end of the trocar 94 is manipulated to position the rod first end proximate to the surgical location or the defective tissue 90. The graspers 96 are then used to remove the needle 102 from its magnetic attachment to the rod end and a stitch is made through the tissue defect 90 at the surgical location. Only one stitch is shown being made in FIG. 6; however, as explained earlier, the surgical instrument of the invention may be employed in forming a line of stitching to close a larger tissue defect. In forming a line of stitching, the needle and attached length of suture are passed through the tissue defect several times along the line in one direction and then are passed again through the tissue defect along a return line back to the position where the suture was first inserted through the tissue. This positions the length of suture extending to the tissue defect from the instrument rod and the length of suture extending from the tissue defect to the needle adjacent each other. With these two lengths of suture positioned adjacent each other a knot may be formed in the suture in the same manner as after forming a single stitch in the tissue defect.

Figure 9:
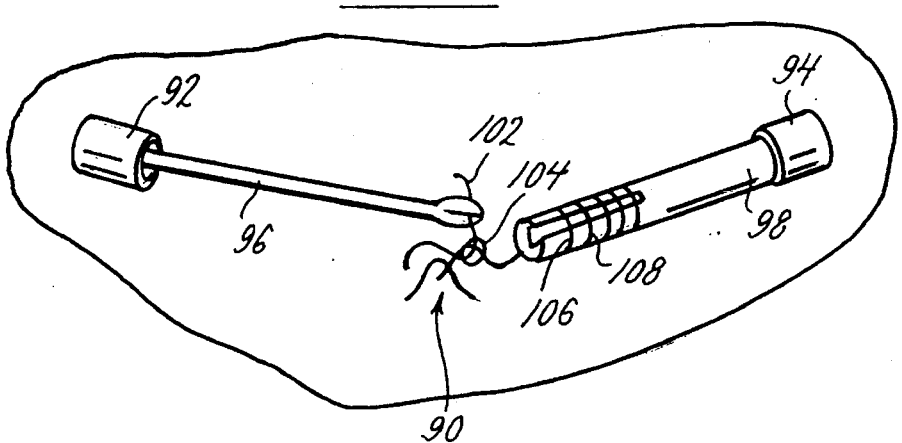
FIG. 9 is a subsequent step to that shown in FIG. 8.
Figure 10:
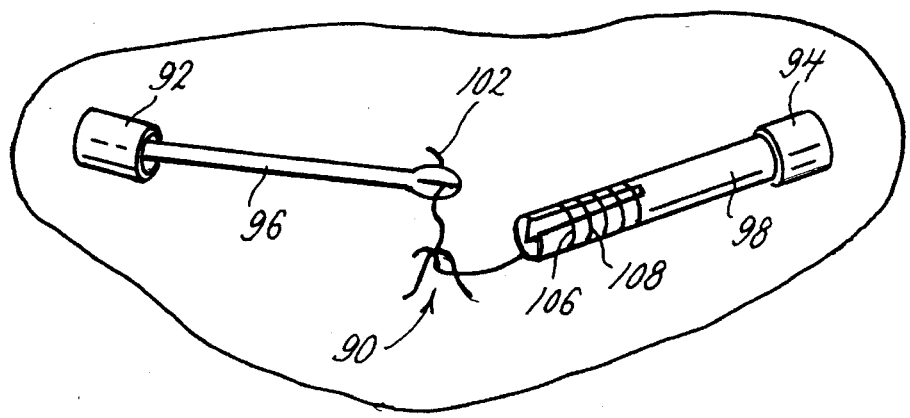
FIG. 10 is a subsequent step to that shown in FIG. 9.

In preparation to form a first throw of a knot in the suture material, the needle is repositioned by the grasper in the slot in the first rod end with the needle extending beneath the first loop 104 of suture material formed on the rod end. FIG. 4 shows in more detail the proper positioning of the needle in preparing to form the first throw of the surgical knot. The needle is held in this position beneath the first loop of the suture by the magnetism of the first rod end. The needle is then released by the grasper 96 and then retaken by the grasper at the distal end of the needle, or the point end of the needle projecting from beneath the first suture loop 104 and out of the slot as viewed in FIG. 8. The needle and attached suture material are then pulled from the instrument slot and from beneath the first suture loop 104 causing the first loop to move off of the first end of the rod as shown in FIG. 9. As the needle and first end of the suture are continued to be pulled away from the rod first end by the grasper, the first loop 104 moves down along the length of suture attached to the needle toward the stitch made at the surgical location in the tissue defect 90, forming a first throw of a knot in the suture material securely closing the stitch, as shown in FIG. 10.

The above process is repeated with the needle and attached suture passing through the slot and beneath the second loop 106 of suture formed on the exterior of the rod first end. As the needle and attached suture are pulled out of the slot and from beneath the second loop 106, the second loop is pulled off the rod first end down the length of suture attached to the needle. As the needle and attached suture are continued to be pulled away from the rod first end, the second loop arrives at the stitch formed by the first throw and forms a second throw of the knot at the stitch. If so desired, the procedure is repeated a third time by inserting the needle beneath the third loop 108 of suture and pulling the needle from beneath the loop and from the rod first end to cause the third loop to move off the rod end and down the suture forming a third throw in the knot at the stitch. This procedure may be repeated as many times as there are suture loops formed on the rod first end to form a knot of any desired number of throws. When the desired knot is formed at the stitch in the surgical location, the two lengths of suture extending from the knot are cut and the knot-tying instrument and needle are removed from the surgical location.

It should be appreciated that the surgical instrument of the invention facilitates tying a knot in a length of suture material at a remote surgical location according to the method of the invention by enabling the positioning of the suture material proximate to the surgical location and by holding the suture material at the surgical location in a manner that enables one or more throws of a knot to be easily formed in the suture material.

Figure 11:
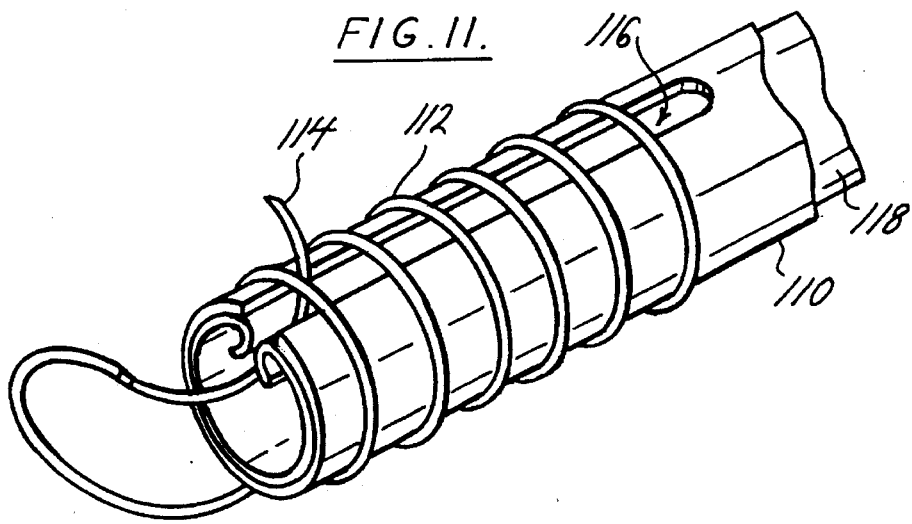
FIG. 11 shows a partial perspective view of a further embodiment of the invention.

FIG. 11 shows a still further embodiment of the rod 110 of the surgical instrument similar to the embodiment shown in FIG. 3. In this embodiment, the rod has substantially the same configuration as the embodiment shown in FIGS. 1 and 4 with the length of suture material 112 and the needle 114 affixed thereto looped over the exterior surface of the rod 110 in substantially the same manner as that described with reference to FIGS. 1 and 4. The rod 110 has a slot 116 formed in its first end in the same manner as the previously described embodiment of FIGS. 1 and 4 and the length of suture material is looped over the slot. Like the FIG. 3 embodiment, in the FIG. 11 embodiment the longitudinal length of the surgical instrument is divided into two sections, with the first section comprising the rod 110 and the second section comprising a tubular handle 118 having a first end inserted through the interior of the rod. As shown in FIG. 11, the rod 110 is detachably secured to the first end of the handle 118 by being slipfit over the end of the handle. The interior diameter of the rod 110 is substantially equal to the exterior diameter of the handle 118 so that the rod 110 may be easily slipfit over the end of the handle 118 and held on the handle end by friction engagement. The rod has a slot 120 that is equal in length to the slot 116 of the rod and is aligned with the rod slot. Like the embodiment of FIG. 3, the longitudinal length of the instrument handle 118 enables it to be used in both deep open incisions or in laparoscopic surgery as in the previously described embodiments. The ability of the rod 110 to be detached from the handle 118 enables the rod to be detached and disposed of after use and replaced on the handle by a like rod. With the configuration of the surgical instrument shown in FIGS. 11 and 12, once the length of suture has been used from one rod 110 of the instrument the used rod may be detached from the handle 118 and replaced with a new rod having a length of suture looped over its exterior surface.

Figure 12:
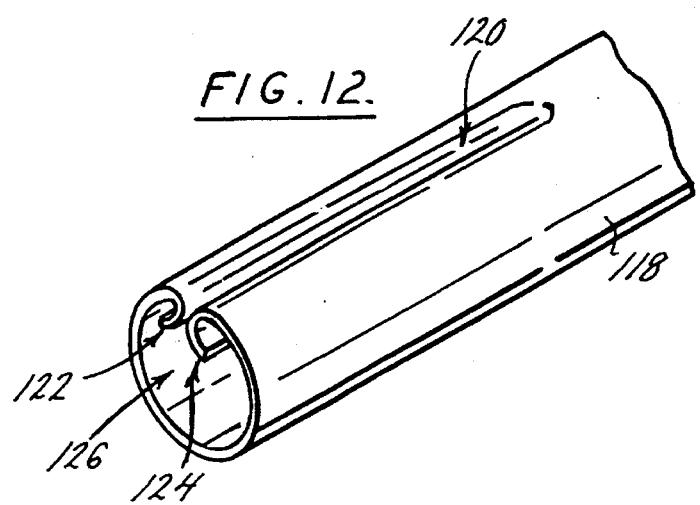
FIG. 12 shows a partial perspective view of a handle used with the embodiment of FIG. 11.

As explained above, the handle slot 120 has a longitudinal length substantially equal to that of the rod slot 116 but is also provided in a specific configuration that enables the handle slot 120 to grip the needle 114 between the opposite lateral ends of the slot. With the handle slot 120 having such an ability, it is no longer necessary to provide a magnetic strip along the slot of the rod 110 to temporarily hold the needle 114 while using the instrument of the invention. As best seen in FIG. 12, the opposite lateral ends 122, 124 of the handle slot 120 are curved underneath and then back toward the interior surface of the handle 118. This gives the handle slot 120 a much narrower width than the slot 116 of the rod 110 enabling it to pinch grip the needle 114 within the slot. The manner in which the opposite lateral ends 122, 124 of the handle slot 120 are bent down into the interior bore 126 of the handle 118 forms a pair of tapered converging surfaces in the underside of the slot 120 that direct the needle 114 into the slot 120 when it is inserted into the handle bore 126 from the handle first end and then upward toward the slot. The tapered surfaces of the underside of the slot 120 direct the tip of the needle 114 inserted into the handle bore 126 upward as viewed in FIG. 12 into the slot 120 thereby facilitating positioning the needle 112 in its gripped stationary position in the slot.

Figure 13:
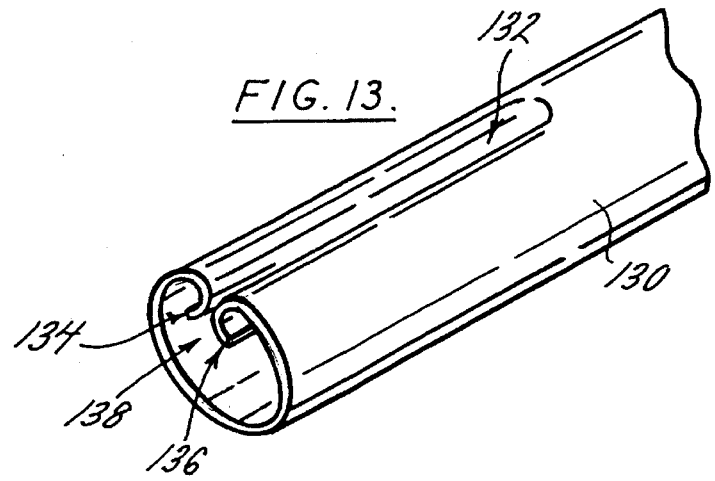
FIG. 13 shows a partial perspective view of a further embodiment of the invention.

A still further embodiment of the rod 130 of the surgical instrument of the invention is shown in FIG. 13. This embodiment of the rod 130 is substantially identical to the first described embodiment of FIGS. 1 and 4 except for the configuration of the rod slot 132. The first end of the rod 130 has the same cylindrical configuration of the first described embodiment of FIGS. 1 and 4 and although not shown, a length of suture material is wrapped over the exterior surface of the rod and the slot 132 with one end of the suture secured to the rod and the opposite end of the suture secured a needle in the same manner as the first described embodiment. The embodiment of FIG. 13 differs from the previously described embodiment of FIGS. 1 and 4 in that the configuration of the slot 132 is substantially identical to that of the just described embodiment of the instrument handle 118 shown in FIGS. 11 and 12. The instrument rod slot 132 is formed with its opposite lateral edges 134, 136 being downturned into the interior bore 138 of the rod to form the slot configuration shown in FIG. 13. The configuration of the rod slot 132 operates in substantially the same manner as described above with regard to the handle slot 120 of FIGS. 11 and 12 to direct the needle inserted into the rod bore 138 upward into the slot and to pinch-grip the needle within the slot. With the configuration of the instrument rod 130 shown in FIG. 13 it would not be necessary to provide a strip magnet adjacent the slot 132 as the function of temporarily holding the needle relative to the rod end is performed by the configuration of the slot itself.

Figure 14:
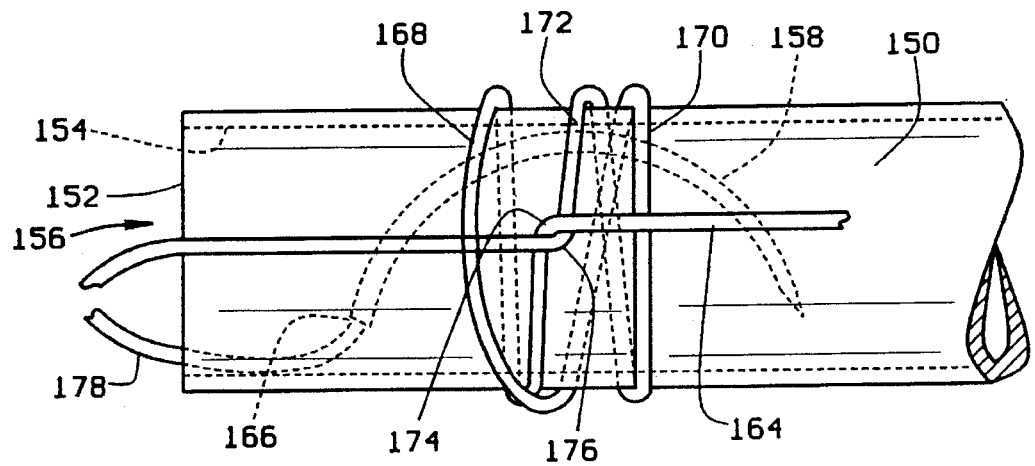
FIG. 14 shows a partial side view of a further embodiment.
Figure 15:
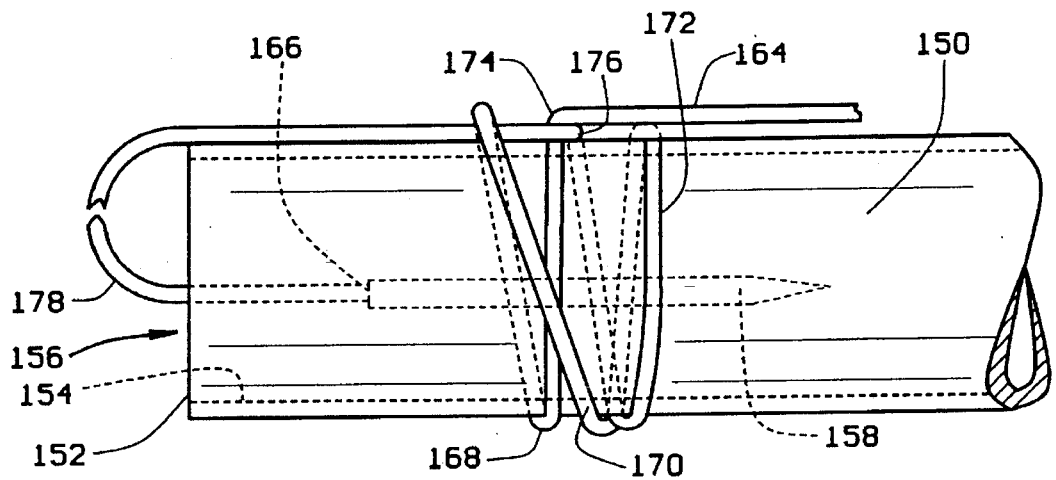
FIG. 15 shows the embodiment of FIG. 14 rotated 90°.
Figure 16:
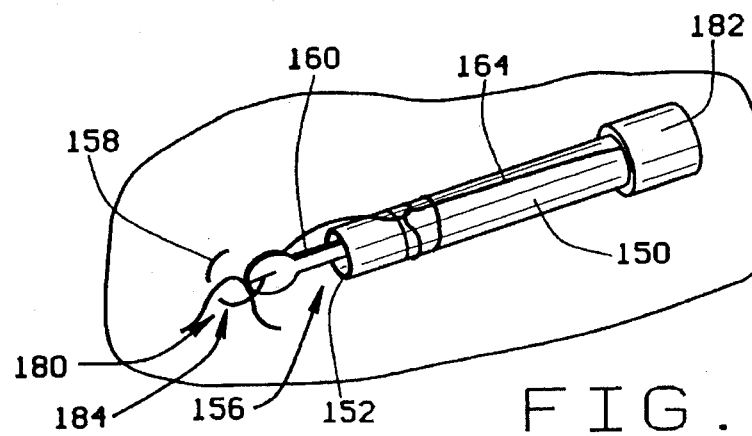
FIG. 16 is a schematic representation of a step involved in the method of use of the FIG. 14 embodiment of the instrument in tying a knot in a length of suture.
Figure 17:
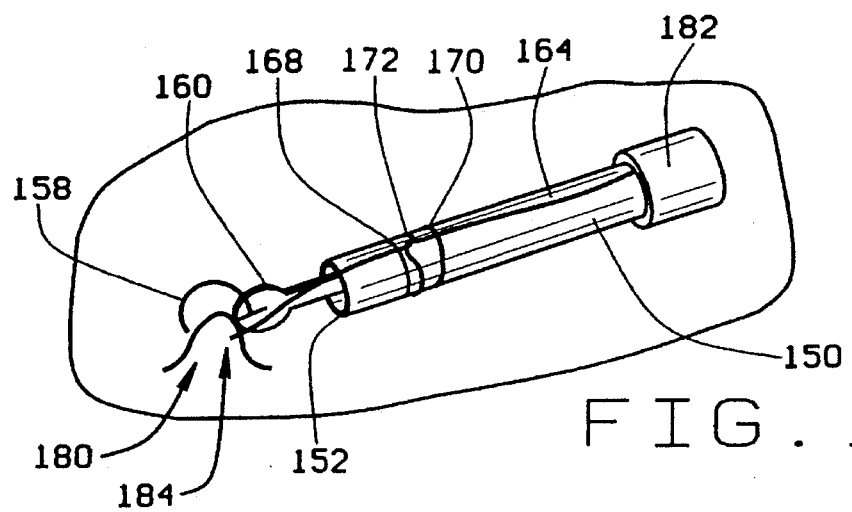
FIG. 17 is a subsequent step to that shown in FIG. 16.

FIGS. 14 and 15 show a still further embodiment of the rod 150 of the surgical instrument of the invention. The rod 150 is similar to the previously described embodiments and includes opposite first 152 and second ends. The second end is not shown in the drawing figures but is substantially identical to the second rod end of the previously described embodiments. A hollow interior bore 154 extends through the rod between its opposite first and second ends. The bore 154 forms an access opening 156 at the first or distal end of the rod. The dimensions of the interior bore 154 are sufficient to enable insertion of a conventional needle 158 into the interior bore as shown in FIG. 14, or the insertion of a conventional laparoscopic grasping instrument 160 through the interior bore as shown in FIGS. 16 and 17. As in the previously described embodiments, the rod 150 may have an axial length sufficient to enable insertion of the rod completely through a cannula 162, with the rod first end 152 projecting from the cannula at one end and the rod second end (not shown) projecting from the cannula at its opposite end, enabling manipulation of the rod first end by manual manipulation of the rod second end. In variant embodiments, the rod 150 may be connected with a hollow handle, similar to the handle 86 shown in FIG. 3, in the same manner as the embodiment of the invention described with reference to FIG. 3. In such an embodiment, manipulation of the rod first end 152 is accomplished by manual manipulation of the rod handle second end projecting from a cannula. The hollow bore of the handle is coextensive with the rod interior bore and enables a surgical grasper to be inserted through both the handle and rod.

With the rod interior bore 154 being dimensioned large enough to accommodate the needle 158 and the insertion of a surgical grasper 160 through the bore, the needle 158 may be retained in position in the interior bore by a grasper 160 inserted through the rod interior bore and grasping the needle adjacent the rod first end. Although dimensions of the rod are described herein, it should also be understood that the dimensions may be varied to best suit the rod for its intended use in the same manner as described with reference to previous embodiments of the invention.

As in the previous embodiments, a length of suture material 164 is secured to the rod 150. The suture material has opposite first 166 and second ends (not shown) with the second end of the suture being secured to the rod 150 adjacent the rod second end in a manner such as that described with reference to the previous embodiments of the invention. The first end 166 of the suture is secured to the needle 158 in a conventional manner. The length of suture 164 extends from the instrument rod second end along the exterior surface of the rod toward the rod first end 152 and is wrapped in several loops 168, 170, 172 at the first end of the rod. In this embodiment of the invention, the pattern in which the suture material is wrapped around the rod differs from that of the previously described embodiments. From the last of the plurality of loops formed in the suture, the suture extends to its first end 166 secured to the needle 158.

The plurality of loops formed in the suture material are wrapped around the exterior surface of the rod in a specific configuration that enables the loops to be manipulated to slide along the longitudinal length of the rod and off the rod first end 152. Although a specific arrangement of the suture material forming the plurality of loops is shown in FIGS. 14 and 15, it should be appreciated that the pattern of loops formed in the suture material may be reversed relative to the rod first end 152 from the pattern shown in FIGS. 14 and 15. The specific configuration of the suture loops 168, 170, 172 shown in FIGS. 14 and 15 is produced by forming a first bend 174 in the suture material as it extends longitudinally over the exterior surface of the rod 150 from the rod second end toward the rod first end 152. From the first bend 174, the suture material extends laterally relative to the rod and is wrapped one complete revolution around the exterior surface of the rod back to the first bend 154, thereby forming the first loop 168. The suture material is then again wrapped one complete revolution around the exterior surface of the rod back to the first bend forming the second loop 170 in the suture material. It should be noted that in forming the second loop 170, the suture material of the second loop is wrapped over the suture material of the first loop 168. From the end of the second loop, the suture material is then again wrapped one complete revolution around the exterior surface of the rod back to the first bend 174, thereby forming the third loop 172. It should be noted that in forming the third loop 172, the suture material forming the third loop is passed beneath the suture material forming the second loop 170. With the arrangement of the three loops of suture material described above, the second loop 170 passes over both the first loop 168 and the third loop 172 as it extends in one complete revolution around the rod 150. This relative position of the second loop 170 to the first 168 and third 172 loops remains the same whether the plurality of loops are formed on the rod 150 in their relative positions shown in FIGS. 14 and 15, or in reversed positions relative to the rod. It should also be noted that at the end of the second loop 170 and the beginning of the third loop 172, the suture material passes beneath the length of suture extending from the suture second end (not shown) to the first bend 174 formed in the suture. From the three loops 168, 170, 172 formed in the suture material, the suture material is then formed in a second bend 176 around the first bend 174 of the suture and again extends longitudinally along a portion of the rod's length toward the rod first end 152, thereby completing the formation of the plurality of loops in the suture material. As the suture material extends from the second bend 176 toward the rod first end 152 it passes beneath the first loop 168 formed in the suture material. The tightness of the first loop 168 around the exterior surface of the rod 150 and over the the portion of the suture extending from the second bend 176 toward the rod first end 152 prevents the plurality of loops formed in the suture material from unraveling.

From the second bend 176, the suture material extends through a portion 178 of its overall length to the needle 158 secured to the first end of the suture. The length of the portion of suture material 178 extending between the second bend 176 and the needle 158 can be varied depending on the particular use intended for the instrument. This portion 178 of the overall length of the suture material can be kept from hanging free from the rod first end 152 by pulling the needle 158 through the rod interior bore 154 from the first end 152 toward the second end of the rod, thereby causing the slack portion of suture material 178 to be pulled around the rod first end 152 and through the rod interior bore 154, taking up the slack in this portion of suture. If so desired, the length of this portion of suture material 178 can be made sufficient to pull the needle 158 completely through the interior bore 154 of the rod from its first end 152 and out of the rod second (not shown) to facilitate attachment of a surgical grasper to the needle prior to insertion of the grasper and attached needle back through the rod bore in use of the instrument. The manner in which the surgical grasper 160 would retain the needle 158 in the rod bore 154 is substantially identical to that of previously described embodiments. In variations of the FIG. 14 and 15 embodiment where the instrument is removably attached to a hollow handle such as that shown in FIG. 3, the surgical grasper would extend through the hollow interior bores of both the handle and the instrument to grip and maintain the needle 158 within the interior bore of the instrument. Again, use of the instrument shown in FIG. 14 with a handle such as that shown in FIG. 3 is substantially identical to that of previously described embodiments.

FIGS. 16 and 17 are schematic representations of the method of the invention employed in using the surgical instrument of the invention shown in FIGS. 14 and 15 for tying a knot in a length of suture in a laparoscopic surgical operation. As in previously described embodiments, the description of the method to follow is illustrative only and should not be interpreted as limiting the use of the surgical instrument of the invention to only laparoscopic surgical techniques or limiting the use to only forming a stitch in securing adjacent tissues together. The benefits provided by the unique surgical instrument of the invention suit it for use in a variety of different known surgical techniques and for use in forming both a single stitch and a line of stitching in body tissues.

FIGS. 16–19 are schematic representations of a view looking inside a body cavity toward an opening in a tissue 180 representing a defect to be repaired or mended by use of the surgical instrument of the invention in accordance with the method of the invention. The drawing figures illustrate a laparoscopic repair of the defect 180 in the tissue and a single trocar or cannula 182 is shown already inserted through the right flank of the body into the cavity. The first end 152 of the surgical instrument rod 150 with the length of suture 164 wrapped thereover and the needle 158 secured to the suture are shown inserted through the trocar 182. A conventional surgical grasper 160 is also shown inserted through the rod interior bore 154 and gripping the needle 158. As in the previously described embodiments, the second end of the rod (not shown) extending from the exterior end of the trocar 182 is manipulated to position the rod first end 152 proximate to the surgical location or the defective tissue 180. The grasper 160 received in the rod interior 154 and gripping the needle 158 is then extended from the interior bore through the opening 156 at the first end of the rod and manipulates the needle 158 to form a stitch 184 through the tissue defect at the surgical location. As explained in previous embodiments, although only one stitch is shown in the drawing figures, the instrument of the invention may be employed in forming a line of stitching in the same manner as the previously described embodiments.

Figure 18:
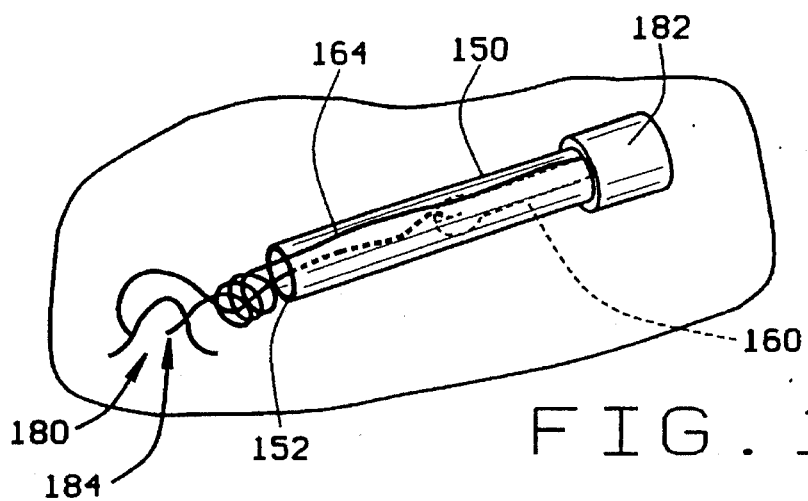
FIG. 18 is a subsequent step to that shown in FIG. 17.
Figure 19:
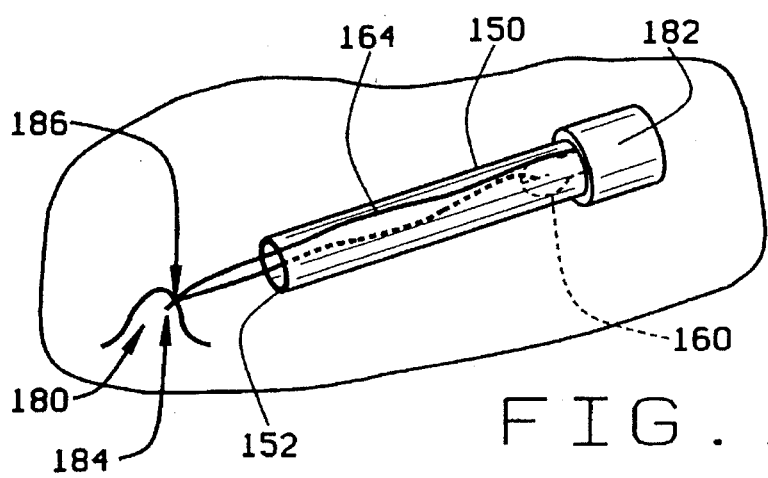
FIG. 19 is a subsequent step to that shown in FIG. 18.

With the needle 158 having been inserted through the tissue defect 180, the grasper 160 is then controlled to release the needle and then grip the needle again adjacent its distal end which has been inserted through the tissue defect. The needle gripped at its distal end is then pulled through the stitch causing a portion of the suture material adjacent to its attachment to the needle to be pulled through the stitch. As shown in FIG. 18, the grasper 160 gripping the distal end of the needle 158 is then pulled back through the interior bore 154 of the rod causing the needle and the portion of suture material attached to the needle to pass through the rod opening 156 and into the rod interior bore.

As the suture is pulled through the stitch in the tissue 180, the length of suture extending between the plurality of loops 168, 170, 172 and the stitch 184 is pulled tight causing the plurality of loops to be pulled longitudinally over the exterior surface of the rod and off the rod first end 152. As shown in FIG. 18, as the plurality of loops 168, 170, 172 are pulled off of the rod at its first end 152, they pass over the portion of the suture attached to the needle 158 being pulled through the rod opening 156 into the rod interior bore 154. As the grasper is continued to be pulled through the rod interior bore from the rod first end 152 toward the rod second end, the suture material is continued to be pulled through the stitch 184, causing the plurality of loops to move toward the stitch and contract as they reach the stitch. The contraction of the plurality of loops around the portion of suture material passed through the body tissue 180 and pulled back into and through the rod interior bore 154 forms a knot 186 closing the stitch and the defect in the body tissue. With the knot 186 having been formed in the stitch 184, the two lengths of suture extending from the knot are cut and the knot-tying instrument and needle held by the grasper in the rod interior are removed from the surgical location.

It should be appreciated that the surgical instrument of the invention shown in FIGS. 14 and 15 facilitates tying a knot in a length of suture material at a remote surgical location according to the method of the invention described above by enabling the positioning of the suture material proximate to the surgical location and by holding the suture material at the surgical location in a manner that enables a knot to be easily formed in the suture material.

While the present invention has been described by reference to a specific embodiment, it should be understood that modifications and variations of the invention may be constructed without departing from the scope of the invention defined in the following claims.

What is claimed is:

1. A surgical instrument for tying a knot in a length of suture, the instrument comprising:

a rod having a longitudinal length with opposite first and second ends and an exterior surface extending between the first and second ends;

a length of suture having opposite first and second ends, the first end of the suture being secured to a needle and the second end of the suture being positioned adjacent the second end of the rod, the length of suture extending from its second to its first end along the rod from the rod second end to the rod first end with at least one loop being formed in the suture and wrapped laterally around the exterior surface of the rod;

a plurality of loops are formed in the suture and are each wrapped laterally around the exterior surface of the rod; and, the plurality of loops are formed in the suture by the length of suture extending longitudinally along the rod from the rod second end toward the rod first end with a first bend being formed in the suture and the suture extending laterally from the first bend making at least one revolution around the exterior surface of the rod back to the first bend, a second bend being formed in the suture around the first bend and the suture extending longitudinally from the second bend toward the rod first end.

2. The instrument of claim 1, wherein:

a handle having opposite first and second ends is attached to the second end of the rod, the handle having an elongated configuration enabling insertion of the rod and handle through a cannula and to enable manipulation of the rod in laparoscopic surgery by manual manipulation of the handle.

3. The instrument of claim 2, wherein:

the first end of the handle is removably attached to the second end of the rod enabling the rod to be removed from the handle and replaced by a like rod removably attached to the handle first end.

4. The instrument of claim 1, wherein:

the longitudinal length of the rod has an elongated configuration that enables insertion of the first end of the rod through a cannula with the second end of the rod projecting from the cannula enabling remote manipulation of the first end of the rod in laparoscopic surgery by manual manipulation of the rod second end.

5. The instrument of claim 1, wherein:

the rod has a hollow interior bore extending between its first and second ends, an opening is provided in the rod first end giving access to the rod interior bore through the opening, the opening being configured to enable insertion of the needle through the opening and through the interior bore.

6. The instrument of claim 5, wherein:

at least one loop formed in the one suture around the exterior surface of the rod is configured to enable the loop to be pulled off the first end of the rod in response to the needle and the suture first end being inserted through the rod opening and pulled through the interior bore of the rod from the rod first end toward the rod second end.

7. The instrument of claim 5, wherein:

at least one loop formed in the one suture around the exterior surface of the rod is configured so that the one loop is pulled off the rod over the rod opening and around a portion of the suture pulled into the rod opening in response to the needle and the portion of the suture being passed through tissue to form a stitch and then pulled back through the rod opening and through the interior bore of the rod from the rod first end toward the rod second end.

8. The instrument of claim 7, wherein:

the at least one the loop formed in the suture is configured so that the one loop, having been pulled off the rod and around the portion of the suture pulled into the rod opening, contracts and forms a knot on the portion of suture passed through the tissue in response to the needle and the portion of the suture being pulled through the rod opening and through the interior bore of the rod from the rod first end toward the rod second end.

9. A surgical instrument for tying a knot in a length of suture, the instrument comprising:

a rod having a longitudinal length with opposite first and second ends and a exterior surface extending between the first and second ends;

a length of suture having opposite first and second ends, the first end of the suture being secured to a needle and the second end of the suture being positioned adjacent the second end of the rod, the length of suture having at least one loop formed therein, the loop being wrapped at least one revolution around the exterior surface of the rod;

means provided on the rod for enabling the needle to be passed through the loop wrapped around the rod pulling the first end of the suture through the loop;

a plurality of loops are formed in the suture and wrapped around the exterior surface of the rod; and, the plurality of loops are formed in the suture by the length of suture extending longitudinally along the rod from the rod second end toward the rod first end, a first bend being formed in the suture adjacent the rod first end, the suture from the first bend being wrapped laterally around the exterior surface of the rod, then a second bend is formed in the suture around the first bend and the suture extends longitudinally toward the rod first end from the second bend.

10. The surgical instrument of claim 9, wherein:

the rod has a hollow interior bore extending between its first and second ends and an opening at the first end providing access to the interior bore, the first end of the rod is configured to cause at least one loop formed in the suture to be pulled off the first end of the rod and onto a portion of the length of suture by the needle and the first end of the suture being passed through the rod opening and one loop wrapped around the rod and pulled through the rod interior from the rod first end toward the rod second end.

11. The instrument of claim 9, wherein:

the longitudinal length of the rod has an elongated configuration that enables insertion of the first end of the rod through a cannula with the second end of the rod projecting from the cannula and enables remote manipulation of the first end of the rod by manual manipulation of the rod second end.

12. The instrument of claim 9, wherein:

a handle is removably attached to the rod second end enabling the rod to be removed from the handle and replaced by a like rod removably attached to the handle, the handle having an elongated configuration enabling insertion of the rod attached to the handle through a cannula with the handle projecting from the cannula and enabling remote manipulation of the rod first end by manual manipulation of the handle projecting from the cannula.

13. The instrument of claim 9, wherein:

the suture from the first bend is wrapped laterally once around the rod forming a first loop, and then is wrapped laterally again around the rod forming a second loop, and then is wrapped laterally again around the rod forming a third loop in the suture, the first, second and third loops all being formed between the first and second bends in the suture.

14. The instrument of claim 13, wherein:

the second loop wrapped around the rod passes over the first and third loops wrapped around the rod.

* * * * *

UNITED STATES PATENT AND TRADEMARK OFFICE
CERTIFICATE OF CORRECTION

PATENT NO. : 5,472,446

DATED : December 5, 1995

INVENTOR(S) : Roger A. de la Torre

It is certified that error appears in the above-indentified patent and that said Letters Patent is hereby corrected as shown below:

Col. 14, line 52, delete "one" (second occurrence);

Col. 14, line 53, following "the" (second occurrence) insert --one--;

Col. 14, line 60, delete "one" (second occurrence).

Signed and Sealed this

Twenty-sixth Day of March, 1996

Attest:

BRUCE LEHMAN

*Attesting Officer*   *Commissioner of Patents and Trademarks*